(12) United States Patent
Hancock et al.

(10) Patent No.: US 12,161,402 B2
(45) Date of Patent: Dec. 10, 2024

(54) ELECTROSURGICAL ENERGY CONVEYING STRUCTURE AND ELECTROSURGICAL DEVICE INCORPORATING THE SAME

(71) Applicant: CREO MEDICAL LIMITED, Monmouthshire (GB)

(72) Inventors: Christopher Paul Hancock, Bath (GB); Shaun Preston, Chepstow (GB); William Taplin, Chepstow (GB); Sam James, Chepstow (GB); George Ullrich, Bangor (GB); David Webb, Bangor (GB)

(73) Assignee: CREO MEDICAL LIMITED, Chepstow (GB)

( * ) Notice: Subject to any disclaimer, the term of this patent is extended or adjusted under 35 U.S.C. 154(b) by 889 days.

(21) Appl. No.: 16/481,384

(22) PCT Filed: Mar. 29, 2018

(86) PCT No.: PCT/EP2018/058112
§ 371 (c)(1),
(2) Date: Jul. 26, 2019

(87) PCT Pub. No.: WO2018/178252
PCT Pub. Date: Oct. 4, 2018

(65) Prior Publication Data
US 2019/0374285 A1    Dec. 12, 2019

(30) Foreign Application Priority Data

Mar. 30, 2017   (GB) ...................................... 1705167

(51) Int. Cl.
*A61B 18/18*   (2006.01)
*A61B 1/00*    (2006.01)
(Continued)

(52) U.S. Cl.
CPC ............ *A61B 18/1815* (2013.01); *A61B 1/07* (2013.01); *A61B 5/0084* (2013.01);
(Continued)

(58) Field of Classification Search
CPC ............ A61B 18/1815; A61B 18/1206; A61B 18/1492; A61B 18/18; A61B 1/07;
(Continued)

(56) References Cited

U.S. PATENT DOCUMENTS 4,960,134 A * 10/1990 Webster, Jr. ............ A61N 1/056
607/116
5,125,896 A *  6/1992 Hojeibane .............. A61N 1/056
604/95.04

(Continued)

FOREIGN PATENT DOCUMENTS

CN        1899212 A      1/2007
CN      101801299 A      8/2010
(Continued)

OTHER PUBLICATIONS

International Preliminary Report on Patentability issued from the International Bureau in counterpart International Application No. PCT/EP2018/058112, mailed on Jul. 8, 2019, (PCT/IPEA/418 & PCT/IPEA/409).

(Continued)

*Primary Examiner* — Khadijeh A Vahdat
*Assistant Examiner* — Marina Delaney Templeton
(74) *Attorney, Agent, or Firm* — ArentFox Schiff LLP

(57) ABSTRACT

An energy conveying structure for invasive electrosurgery that provide for combined delivery of (i) RF or microwave electromagnetic energy for tissue treatment (e.g. ablation, coagulation or cutting), and (ii) optical radiation within a common structure that may form an instrument cable of a surgical scoping device. The structure resembles a hollow (Continued)

coaxial transmission line with an optical channel formed within it. The optical channel can lie within a passage that is formed within the inner conductive layer or within other layers of the coaxial transmission. The structure may be used to form an electrosurgical device capable of delivering RF/microwave EM energy, optical radiation and ultrasonic signals to a treatment site along an instrument cable of a surgical scoping device.

30 Claims, 6 Drawing Sheets

(51) Int. Cl.
    A61B 1/07   (2006.01)
    A61B 5/00   (2006.01)
    A61B 18/00  (2006.01)
    A61B 18/12  (2006.01)
(52) U.S. Cl.
    CPC ...... *A61B 18/1206* (2013.01); *A61B 1/00165* (2013.01); *A61B 2018/00589* (2013.01); *A61B 2018/00601* (2013.01); *A61B 2018/00636* (2013.01); *A61B 2018/00982* (2013.01); *A61B 2018/00994* (2013.01); *A61B 2018/126* (2013.01); *A61B 2018/1861* (2013.01)
(58) Field of Classification Search
    CPC .............. A61B 1/00165; A61B 5/0084; A61B 2018/00994; A61B 2018/00589; A61B 2018/00636; A61B 2018/00982; A61B 2018/126; A61B 2018/0091; A61B 2018/183; A61B 2018/1838; A61B 2018/1853; A61B 2018/00577; A61B 2018/1876; A61B 2018/1846; A61B 2018/1861; A61B 2018/1884; A61B 2018/1892; A61B 2017/2927; A61B 2017/00473; A61B 2017/003; A61B 2017/00309; A61B 2017/00867; A61B 2017/00318; A61B 2090/037; A61B 17/3421; A61M 25/0105; A61M 25/0133; A61M 25/0147; A61M 25/0138; A61M 25/0136; A61M 2025/015; A61M 2025/0681
    See application file for complete search history.

(56)             References Cited

U.S. PATENT DOCUMENTS

| | | | | |
|---|---|---|---|---|
| 5,201,730 | A * | 4/1993 | Easley | A61B 18/1402 604/20 |
| 5,228,441 | A * | 7/1993 | Lundquist | A61B 18/1492 607/116 |
| 5,322,064 | A * | 6/1994 | Lundquist | A61M 25/0051 607/122 |
| 5,467,420 | A * | 11/1995 | Rohrmann | G02B 6/3817 385/101 |
| 5,702,433 | A * | 12/1997 | Taylor | A61M 25/0144 604/22 |
| 6,723,084 | B1 | 4/2004 | Desinger | |
| 6,723,094 | B1 * | 4/2004 | Desinger | A61B 18/14 606/41 |
| 7,142,903 | B2 * | 11/2006 | Rodriguez | A61B 5/287 600/374 |
| 7,799,019 | B2 * | 9/2010 | Turovskiy | A61B 18/18 606/33 |
| 8,506,562 | B2 * | 8/2013 | Anderson | A61M 25/0147 604/95.04 |
| 2003/0100894 | A1 * | 5/2003 | Mahon | A61B 18/1815 606/41 |
| 2006/0119361 | A1 * | 6/2006 | Karmarkar | G01R 33/287 324/322 |
| 2006/0259024 | A1 * | 11/2006 | Turovskiy | A61B 18/1815 606/33 |
| 2007/0249899 | A1 | 10/2007 | Seifert | |
| 2011/0190760 | A1 * | 8/2011 | Niver | A61B 90/37 606/33 |
| 2013/0289557 | A1 * | 10/2013 | Hancock | H01Q 13/08 606/33 |
| 2015/0094656 | A1 * | 4/2015 | Salahieh | A61M 25/0141 604/95.04 |
| 2015/0157405 | A1 * | 6/2015 | Beeckler | A61B 18/1492 606/13 |
| 2016/0278615 | A1 * | 9/2016 | Kawula | A61B 1/00016 |
| 2016/0317218 | A1 * | 11/2016 | Sigmon, Jr. | A61B 18/1492 |

FOREIGN PATENT DOCUMENTS

| | | |
|---|---|---|
| CN | 204351789 U | 5/2015 |
| CN | 106999243 A | 8/2017 |
| DE | 4432666 A1 | 3/1996 |
| GB | 2 414 679 A | 12/2005 |
| WO | WO 2004/073505 A2 | 9/2004 |
| WO | WO 2009/039093 A2 | 3/2009 |
| WO | WO 2011/025640 A1 | 3/2011 |
| WO | WO 2016/059209 A1 | 4/2016 |
| WO | WO 2017/103209 A1 | 6/2017 |

OTHER PUBLICATIONS

International Search Report and Written Opinion, issued by International Searching Authority in corresponding International Application No. PCT/EP2018/058112, mailed on Jun. 19, 2018, (PCT/ISA/210, PCT/ISA/220 & PCT/ISA/237).

Search Report under Section 17(5), Issued in counterpart British Patent Application No. GB1705167.3, dated Aug. 17, 2017.

Written Opinion from the International Preliminary Examining Authority issued from the International Bureau In counterpart International Application No. PCT/EP2018/058112, mailed on Feb. 20, 2019, (PCT/IPEA/408).

* cited by examiner

ELECTROSURGICAL ENERGY CONVEYING STRUCTURE AND ELECTROSURGICAL DEVICE INCORPORATING THE SAME

CROSS-REFERENCE TO RELATED APPLICATIONS

This application is a National Stage entry of International Application No.: PCT/EP2018/058112, filed Mar. 29, 2018, which claims priority to Great Britain Patent Application No. 1705167.3, filed Mar. 30, 2017. The disclosures of the priority applications are hereby incorporated in their entirety by reference.

FIELD OF THE INVENTION

The invention relates to an electrosurgical device for use in minimally invasive procedures, e.g. endoscopy, gastroscopy, bronchoscopy, laparoscopy, etc. In particular, the invention relates to an energy conveying structure (e.g. waveguide or cable) for carrying radiofrequency (RF) and/or microwave energy from an electrosurgical generator along an instrument cable that is insertable into a patient's body to reach a treatment site. The invention may find particular use in natural orifice transluminal endoscopic surgery (NOTES).

BACKGROUND TO THE INVENTION

Conventional surgical scoping devices comprise an insertion tube that can be manoeuvred to a treatment site in a patient's body via a catheter or natural orifice. The insertion tube conveys components to the treatment site. In some examples, the insertion tube comprises an observation channel for conveying an illumination signal and returning an imaging signal, and a separate instrument channel for conveying an instrument for manipulating or otherwise treating tissue at the treatment site. It can be desirable to have real-time vision of the treatment site during treatment.

Electrosurgical instruments are instruments that are used to deliver radiofrequency and/or microwave frequency energy to biological tissue, for purposes such as cutting biological tissue or coagulating blood. Radiofrequency and/or microwave frequency energy is typically supplied to the electrosurgical instrument using a cable. Conventional cables used for this purpose have a coaxial transmission line structure comprising a solid or multi-wire cylindrical inner conductor, a tubular layer of dielectric material around the inner conductor, and a tubular outer conductor around the dielectric material.

When operating many electrosurgical instruments it is common to need to provide additional supplies or components (e.g. control means) to the electrosurgical instrument, such as a liquid or gas feed, liquids or gases, or guide- or pull-wires for manipulating (for example opening/closing, rotating or extending/retracting) part(s) of the electrosurgical instrument.

In order to provide these additional supplies or components to the electrosurgical instrument, additional structures have been provided together with the conventional cable, such as additional tubes adjacent to the conventional cable. For example, it is known to provide an additional tube housing a pull-wire for the electrosurgical instrument alongside the conventional cable, and to house the conventional cable and the tube housing the pull-wire within a single protective jacket/casing.

Typically, the diameter of an instrument channel of a surgical scoping device (e.g. endoscope or laparoscope) is less than 3 mm, e.g. 2.8 mm. It is an ongoing challenge to provide both sufficient power and the additional supplies or components mentioned above in a compact enough form to fit within an instrument channel whilst maintaining flexibility and restricting power loss to acceptable (i.e. safe) levels.

SUMMARY OF THE INVENTION

At its most general, the present invention proposes the combined delivery of RF or microwave electromagnetic energy for tissue treatment (e.g. ablation, coagulation or cutting) and optical radiation within a common structure that may form an instrument cable of a surgical scoping device. The advantages of the invention are threefold. Firstly, the common structure provides a more compact arrangement for systems in which it is desirable to visualise electrosurgical treatment. Secondly, it can enable functionality associated with optical radiation (e.g. imaging or other forms of sensing) to be available on surgical scoping devices without a dedicated observation channel. Thirdly, it can enable the provision of a new family of ultra-small diameter surgical scoping devices which opens up the possibility of electrosurgical treatment in regions that are inaccessible to conventional instruments.

In one example, the common structure may be compact to enable visually-assisted ablation of biological tissue to occur in regions that are inaccessible to conventional surgical scoping devices. However, the use of optical radiation discussed herein need not be confined to providing images of the treatment site. The optical radiation can be used to probe the treatment site to measure properties thereof for diagnostic purposes. For example, the invention may be used to provide laser scattering measurements/spectroscopy, UV reflectometry/scattering measurements, etc.

The term "optical radiation" used herein may relate to electromagnetic radiation having a free space wavelength in the range 100 nm to 1 mm. In some embodiments, the optical radiation is in the visible spectrum, where it can be used to illuminate the treatment site and provide visual assistance for an operator. The optical radiation may be broadband, e.g. from a white light source. In other examples, the optical radiation may be narrow band or may have specific wavelengths for detecting or probing certain tissue characteristics. For example, green and blue wavelengths may be selectively applied to the tissue for inspection during an endoscopy procedure. Wavelengths of 415 nm and 540 nm may be preferred. Visualisation of the different layers is possible due to the difference in penetration depth of each wavelengths. 415 nm light is used to show the capillaries in the mucosa whilst 540 nm allows visualisation of the blood vessels in deeper layers.

In some examples, the common structure may further include means for transmitting ultrasonic signals, e.g. from a distal instrument tip to one or more ultrasonic sensors in a handpiece. The common structure may thus be used to form an electrosurgical device capable of delivering any or all of RF/microwave EM energy, optical radiation and ultrasonic signals to a treatment site along an instrument cable of a surgical scoping device.

According to the invention, there is provided an energy conveying structure for invasive electrosurgery, the energy conveying structure comprising a coaxial layered structure having: an inner conductive layer; an outer conductive layer formed coaxially with the inner conductive layer; and a dielectric layer separating the inner conductive layer and the outer conductive layer, wherein the inner conductive layer, the outer conductive layer and the dielectric layer form a coaxial transmission line for conveying radiofrequency (RF) and/or microwave electromagnetic (EM) energy, wherein the inner conductive layer is hollow to form a longitudinal passage, and wherein the energy conveying structure further comprises an optical channel for conveying optical radiation, the optical channel being located in the longitudinal passage. The energy conveying structure thus resembles a hollow coaxial transmission line with an optical channel formed within it. In this example, the optical channel lies within a passage that is formed within the inner conductive layer. In other examples, the optical channel may lie within a passage formed within other layers of the coaxial layered structure, e.g. the dielectric material or the outer conductor layer. The optical channel may be annular. The optical channel may be the dielectric material of the coaxial layered structure.

With the arrangement defined above, the energy conveying structure can deliver RF/microwave energy for treatment (e.g. ablation) and optical radiation for sensing or visualising the treatment site in a particularly compact manner. The coaxial layered structure may comprise an innermost insulating layer between the inner conductive layer and the optical channel. The innermost insulating layer may prevent interference between the optical channel and the coaxial transmission line.

In this specification "microwave" may be used broadly to indicate a frequency range of 400 MHz to 100 GHz, but preferably the range 1 GHz to 60 GHz. Specific frequencies that have been considered are: 915 MHz, 2.45 GHz, 3.3 GHz, 5.8 GHz, 10 GHz, 14.5 GHz and 24 GHz. In contrast, this specification uses "radiofrequency" or "RF" to indicate a frequency range that is at least three orders of magnitude lower, e.g. up to 300 MHz, preferably 10 kHz to 1 MHz.

References herein to a "conductor" or "conductive" material herein are to be interpreted as meaning electrically conductive unless the context makes clear that another meaning is intended.

The energy conveying structure may be dimensioned to be insertable in a flexible insertion tube of an invasive surgical scoping device. For example, it may have a maximum outer diameter equal to or less than 3.5 mm, preferably equal to or less than 2.8 mm. Herein, the term "surgical scoping device" may be understood as a generic term that refers to a class of devices used in minimally invasive procedures, where the device typically include a rigid or flexible instrument cord that is insertable into a patient's body. The instrument cord is used to provide access to a treatment site for a variety of reasons, e.g. to perform surgical procedures, perform visual inspection or capture images, take biopsies, etc. Examples of a surgical scoping device include an endoscope, a bronchoscope, a laparoscope and the like.

The energy conveying structure may itself form an instrument cable for a surgical scoping device. In this example, the coaxial layered structure may comprise a protective sheath on the outer surface of the outer conductive layer. The protective sheath may be made from biocompatible material or may have a biocompatible coating.

The protective sheath may contribute to steerability of the structure. For example, the protective sheath may comprise a distal portion and a proximal portion, wherein the proximal portion is configured to have greater rigidity than the distal portion. The proximal portion may comprises an additional stiffening layer or braiding to inhibit flexing or deformation.

The optical channel may comprise one or more optical fibres for conveying optical radiation. The optical channel may be configured in a similar manner to the instrument cable of a conventional fiberscope. For example, the optical channel may comprise an illumination optical fibre bundle for conveying an illumination signal along the optical channel in a first direction. Additionally or alternatively, the optical channel may comprises an imaging optical fibre bundle for conveying an imaging signal along the optical channel in a second direction. The optical channel may thus facilitate bidirectional communication of optical radiation along the energy conveying structure.

The energy conveying structure may be used within an electrosurgical device for performing invasive electrosurgery. The electrosurgical device may comprise a handpiece suitable for holding by a operator. The handpiece may comprises a housing that contained components for controlling the electrosurgical device. The handpiece may be connected to a proximal end of an instrument cable. The instrument cable may extend away from the handpiece in a distal direction. The instrument cable may comprise or consist of an energy conveying structure as set out above. An instrument tip may be mounted at a distal end of the instrument cable. The instrument tip may be connected to the coaxial transmission line in the energy conveying structure and arranged to deliver the radiofrequency (RF) and/or microwave EM energy received from the energy conveying structure to surrounding biological tissue located at a treatment site. The instrument cable may be flexible to enable it to be inserted into a patient's body. The instrument cable may have any suitable length for reaching a desired treatment site. For example, it may have a length equal to or greater than 50 cm, and preferably equal to or greater than 1 m.

As explained in more detail below, the handpiece may operably connected to both the coaxial transmission line and the optical channel. The optical channel may extend through a bore in the instrument tip to enable optical radiation to be delivered to or received from the treatment site. In one example, the optical channel may terminate at an aperture formed in an outer surface of the instrument tip.

The instrument tip may comprises any suitable structure for enabling the RF/microwave EM energy to be delivered (e.g. launched) into biological tissue at the treatment site. The instrument tip may comprise a radiating structure (e.g. an antenna or the like) for transferring or coupling microwave energy into surrounding biological tissue. The instrument tip may further comprise a bipolar structure suitable for delivering RF energy. In one example, the instrument tip may comprise a piece of dielectric material, where the inner conductive layer extends longitudinally into the piece of dielectric material beyond a distal end of the outer conductive layer. This structure may provide a radiating antenna for the microwave EM energy. The shape of the piece of dielectric material may be selected based on simulations to achieve efficient delivery of energy. For example, the piece of dielectric material may be a cylindrical piece of ceramic with a rounded distal tip.

The handpiece may comprise a light source for generating an illumination signal to be conveyed along the optical channel. The light source may be a detachable unit, to allow different types of source to be used depending on the treatment scenario. Alternatively or additionally, the handpiece may include an input optical port for receiving optical radiation from a remote source, e.g. a laser or the like, via an optical cable.

The light source may be a light emitting diode (LED), laser diode, or other compact source. The light source may be powered by a power source located in the handpiece, so that the device is portable.

The handpiece may comprise one or more optical elements arranged to optically control or manipulate optical radiation transmitted into or received from the optical channel. For example, the optical elements may comprises one or more lens arranged to shape and direct optical radiation from the light source, e.g. to send it as an illumination signal in along an illumination optical fibre bundle in the optical channel. Additionally or alternatively, the one or more optical elements may comprise one of more lens arranged to capture an image of the treatment site, e.g. from an imaging optical fibre bundle in the optical channel. The imaging optical fibre bundle may include a lens at the instrument tip, e.g. a microlens mounted in the aperture of the instrument tip. The one or more optical elements may be adjustable, e.g. to enable an image signal to brought into focus at an image sensor.

In one example, the device may comprise a integrated fiberscope. In other words, the handpiece may comprise a fiberscope body, and the optical channel may comprises an insertion tube of the fiberscope. The device may thus provide functionality associated with conventional fiberscope systems.

The handpiece may comprise a steering mechanism for controlling an orientation of a distal portion of the instrument cable. The steering mechanism may be controlled form the handpiece through manipulation of a actuator. For example, the actuator may be a rotatable handle or knob, a slider, a dial or the like. The actuator may be mounted on an outer surface of the handpiece to be easily accessible for an operator.

The steering mechanism may comprise a pull arm operably coupled to the actuator to slide within the handpiece. The pull arm may be coupled to the actuator via a movement conversion structure, such as a rack and pinion mechanism, gear mechanism or the like. The steering mechanism may further include a control element extending along the instrument cable, where the control element is operably coupled to the pull arm and the distal portion of the instrument cable. The control element may thus be a component that transfers movement of the pull arm into a deflection of the instrument cable at its distal end.

The control element may comprises a protective sheath that surrounds the coaxial layered structure, e.g. the protective sheath described above. The protective sheath may be anchored to the coaxial layered structure at the distal portion of the instrument cable and may be free to move relative to the coaxial layered structure at the handpiece. Meanwhile, the coaxial layered structure may be anchored to the handpiece. As a result movement of the pull arm relative to the handpiece introduces a relative force between the protective sheath and the coaxial transmission line, which causes deflection of the instrument cable.

The protective sheath may be more rigid in a proximal portion than in a distal portion to provide a preferential deflection zone in the distal portion. Moreover, the protective sheath may have a cut-out portion at one side thereof in the distal portion of the instrument cable. The cut-out portion may act as a living hinge to cause deflection of the distal portion to occur preferentially in one direction. An operator may thus know in advance how the instrument tip will move when the steering mechanism is actuated.

In another example, the control element may comprise one or more control wires that are attached to the pull arm and secured to the instrument cable at the distal portion thereof. The control wires may be any suitable structure for transmitting a force to the distal portion. The control wires may extend longitudinally through the protective sheath that surrounds the coaxial layered structure. For example, the protective sheath may comprises a multi-lumen tube, e.g. having a first (primary) lumen for the coaxial transmission line/optical channel combination and a second (subsidiary) lumen for a control wire.

In a further example, the steering mechanism may not require the protective sheath. For example, the one or more control wires may extend longitudinally through the dielectric layer of the coaxial transmission line.

The handpiece may comprise a power source, such as a rechargeable cell or the like. The power source may be arranged to provide power for components contained in the handpiece, e.g. for any or all of the light source discussed above, and the controller, image sensor and communication module discussed below.

The handpiece may comprise a housing for enclosing its internal components. The housing may be a rigid casing, e.g. may of an insulating material, that encapsulates the components. The casing may have one or more apertures to allow an operator to interact with the components where necessary.

The instrument cable may be detachable from the handpiece. The instrument cable may thus be constructed as a disposable product.

As discussed above, the device may be further configured to deliver ultrasonic energy at the treatment site. Thus, in one example, the instrument tip may comprise an ultrasonic transducer arranged to couple an ultrasonic signal into biological tissue. The ultrasonic transducer may comprise a piezoelectrically active ceramic, e.g. fabricated as part of or within the instrument tip. The instrument cable may be arranged to convey a voltage signal for controlling the piezoelectrically active ceramic to generate the ultrasonic signal. The voltage signal may be conveyed by the coaxial transmission line.

The optical channel of the electrosurgical device may be used as the basis for optical sensing or measurement at the treatment site. This functionality may include using visible radiation to illuminate the treatment site to enable it to be viewed before, during and after treatment. However, this functionality also allows the device to measure properties of tissue at the treatment site, e.g. to enable a diagnostic analysis to be performed before treatment starts.

The handpiece may comprise an optical sensor for detecting optical radiation received into the handpiece from the optical channel. There may be a plurality of optical sensors in the handpiece, e.g. to enable different types of measurement to be taken. The optical sensor may be any suitable device for converting received optical radiation into an output signal indicative of information at the treatment site. In one example, the optical sensor is an image sensor (e.g. a digital camera or the like) for generating an digital image of a treatment site located at a distal end of the optical channel based on an imaging signal received into the handpiece from the optical channel. In other examples, the optical sensor may be a CMOS-based or CCD-based sensor for detecting a measurement signal returned from the treatment site.

The handpiece may comprise a controller having a processor and memory with software instructions stored thereon, which, when executed by the processor, enable the controller to control operation of the device. For example, the controller may control operation of the light source and optical sensor. The processor may be arranged to collect and store information from the optical sensor.

In some examples, the processor may process, e.g. analyse or otherwise manipulate the output signal from the optical sensor. However, in a preferred embodiment the device is arranged to communicate the output signal to a remote device. For example, the handpiece may comprises a communication module arranged to communicate information relating to the detected optical radiation to the remote device. The communication module may comprise a transceiver or network adapter for broadcasting or otherwise communicating the output signal in a wireless manner. For example, the communication module may be arranged to upload image data to a remote server.

The electrosurgical device may be provided as part of an electrosurgical apparatus that further comprises a display device arranged to receive and display the information relating to the detected optical radiation. The display device can be any suitable computing device, e.g. a laptop computer, tablet computer, or smartphone. The display device may be communicably connectable directly or indirectly with the device, e.g. via the communication module. In one example, the display device may be a network-enabled device with permission to access the site to which image data is uploaded by the communication module.

The electrosurgical device may be provided as part of an electrosurgical system that further comprises an electrosurgical generator arranged to generate RF and/or microwave EM energy. The handpiece may be connected to the generator to receive the RF and/or microwave EM energy and couple it into the coaxial transmission line in the instrument cable.

BRIEF DESCRIPTION OF THE DRAWINGS

Examples of the invention are discussed in detail below with reference to the accompanying drawings, in which.

DETAILED DESCRIPTION; FURTHER OPTIONS AND PREFERENCES

Figure 1:
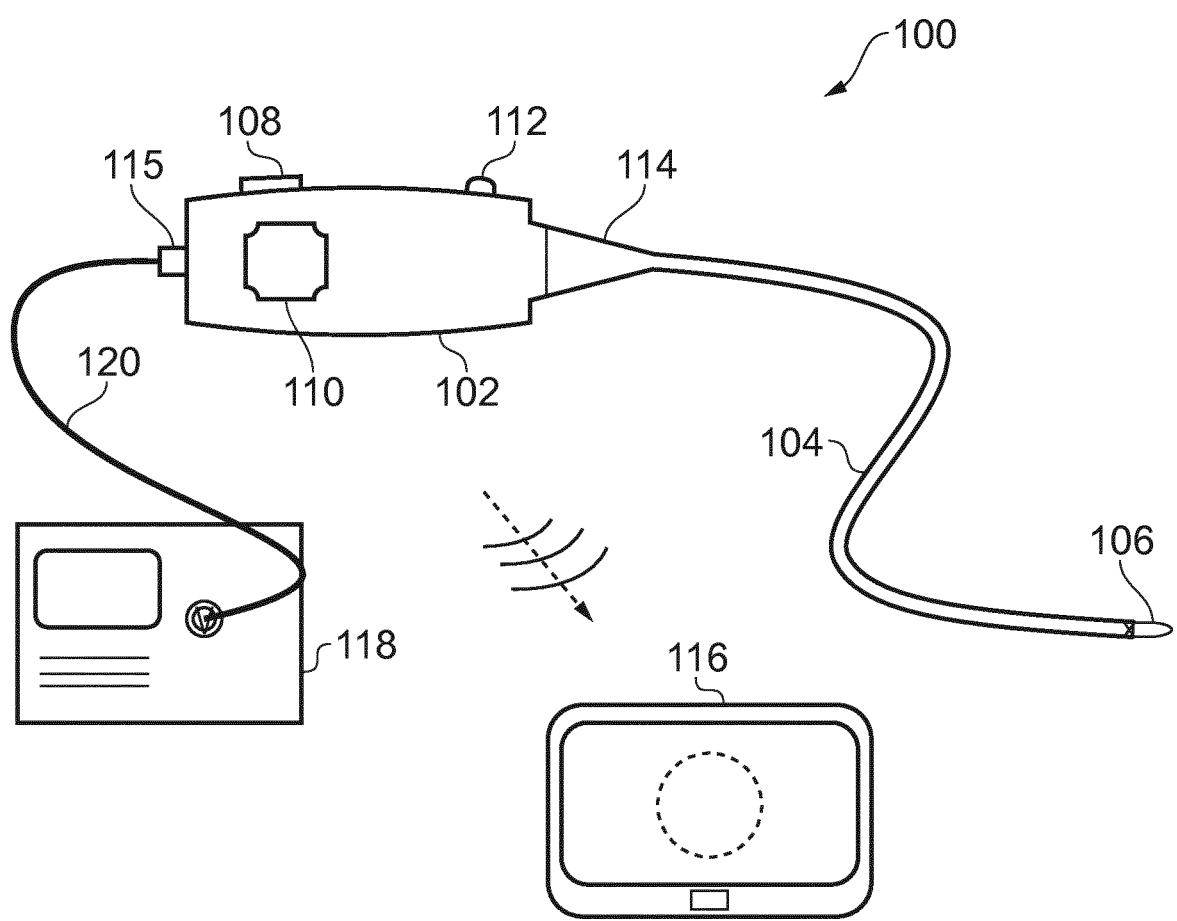
FIG. 1 is a schematic diagram of an electrosurgical apparatus that is an embodiment of the invention.

FIG. 1 is a schematic view of an electrosurgical apparatus 100 according to the present invention. The electrosurgical apparatus 100 comprises a handpiece 102 and a flexible instrument cable 104 extending away from the handpiece 102 in a distal direction. The flexible instrument cable is suitable for insertion into the body to access a treatment site. The flexible instrument cable 104 may have a biocompatible coating on its external surface so that it can be directly inserted into tissue. The instrument cable 104 may be introduced percutaneously or in a minimally invasive manner via a natural orifice. In some examples, the instrument cable 104 may be used with a separate surgical scoping device (not shown), such as an bronchoscope, endoscope, laparoscope or the like. In other examples, the instrument cable may be introduced through a guiding catheter. However, it may be particular advantageous for the instrument cable to be inserted directly (i.e. without surrounding components) to enable it to reach regions of the body that are difficult to access.

The instrument cable 104 in the invention has two functions: carrying microwave electromagnetic (EM) energy and/or radiofrequency (RF) EM energy to the treatment site, and carrying optical radiation for the purposes of imaging or sensing properties of the treatment site. As explained in more detail below, the instrument cable 104 of the invention provides these two functions in a particularly compact manner, by combining the two functions with in a common structure. In a particular example, a optical channel for conveying optical radiation to and/or from the treatment site may be provided within an energy conveying means for the microwave and/or RF electromagnetic (EM) energy. In one example, the optical channel may act as an observation channel arranged to carry optical signals to and from the treatment site to enable an image of the treatment site to be output from the handpiece 102. The handpiece may include an observation port (not shown) for viewing the image. However, in a preferred arrangement, the handpiece 102 may be arranged to transmit the image to a separate display device 116. The image may be transmitted via a wireless connection, e.g. via WiFi or any other suitable networked communication configuration. The display device 116 may be any device with a display screen that is capable of receiving image data. The display device 116 may be portable, e.g. a laptop or tablet computer, a smartphone, or the like. The apparatus of the invention may include the display device, so that the benefits of the invention can be used in locations that do not have local display facilities.

An electrosurgical generator 118 is connected to the handpiece 102 via a cable 120 (e.g. a coaxial cable) which carries the RF and/or microwave energy into the handpiece 102. The generator 118 may be of the type described in WO 2012/076844, for example. The handpiece 102 comprising a connector port 115, which may be a QMA connector port or the like. The connector port 115 may be arranged to electrically connect the cable 120 to an energy conveying structure in the instrument cable 104. This electrical connection may be provided by a "T" connection between a coaxial cable from the generator and a coaxial transmission line of the energy conveying structure. Preferably there is a filter or choke between the "T" junction and an instrument port on the generator to prevent microwave leakage to the instrument port. This must be placed at half a wavelength at the microwave frequency from the "T" junction so that the "T" junction has a high return loss, i.e. does not reflect a significant proportion of the microwave energy back to the generator. The proximal end of the transmission line in the energy conveying structure is open circuit if RF energy is to be transmitted so as not to short out the RF voltage. It is also insulated and protected so that it does not break down for RF voltages or expose the operator to high RF voltages.

The instrument cable 104 has at its distal end an instrument tip 106 that is arranged to receive the RF and/or microwave energy from the energy conveying means in the insertion cable 104. The instrument tip 106 includes an energy delivery portion for delivering the received RF and/or microwave energy into biological tissue, e.g. to assist in treatment, e.g. cutting or coagulation.

The distal end of the instrument cable 104 may be steerable, e.g. to facilitate location of the instrument tip 106 in a desired position for treatment, and/or to enable optical radiation to be directed as desired, e.g. to obtain images of different parts of the treatment site or to take measurements in different positions. As explained below, in some examples the instrument cable 104 may include one of more control elements (e.g. e.g. pull/push rods or control wires) to facilitate steering. The control elements may pass out of a proximal end of the instrument cable to engage a steering mechanism mounted within the handpiece 102. The steering mechanism may be operable to extend and retract the control elements to effect action at the instrument tip. The steering mechanism may include an actuator mounted on the handpiece 102. In this example, the actuator is a rotatable knob 110. Rotation of the knob 110 relative to the housing can be converted to linear motion of the control element(s) via a suitable conversion mechanism mounted in the handpiece 102. One example of a steering mechanism is discussed below with reference to FIG. 7.

To limit the angle at which the proximal end of the instrument cable 104 can be bent relative to the handpiece 102, a conical restrictor 114 is fitted over the proximal end of the instrument cable 104. The conical restrictor 114 is secured to a distal end of the handpiece 102 and thus limits the movement of the cable to prevent it from experiences unwanted stresses.

As discussed in more detail below, the handpiece 102 comprises a housing that contains components associated with generating and controlling the optical radiation that can be conveyed along the optical channel in the instrument cable 104. For example, the handpiece 102 may contain a power source, such as a cell or other battery, an optical source, such as a light emitting diode (LED) or the like, and one or more optical elements for directing optical radiation from the optical source or from the treatment site in a desired manner. The optical elements may include a control interface 112 on the outer surface of the housing, to enable a user to control the optical elements in use. For example, the control interface 112 may control an intensity optical radiation delivered to the treatment site, or may control one or more lenses to assist in focussing an image signal received from the treatment site on to an optical sensor. In one example, an optical detector (e.g. a camera or the like) may be mounted in the handpiece to receive optical radiation returned from the treatment site in order to capture and transmit an image signal to the display device 116. In one example, the optical components may resemble a conventional fiberscope.

The handpiece 102 may include a power switch (not shown) for activating and deactivating the apparatus. The handpiece 102 may include a charging port (not shown) for connecting the power source to an external power supply to enable it to be recharged.

Figure 2:
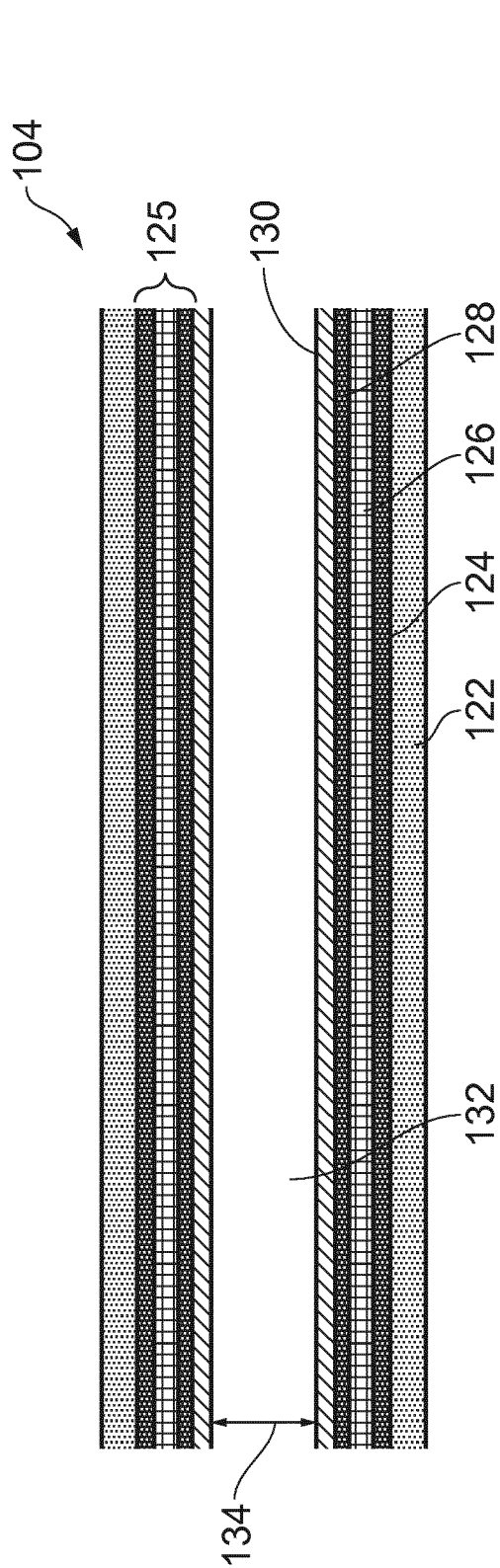
FIG. 2 is a schematic cross-sectional view through an instrument cable for an electrosurgical apparatus that is an embodiment of the invention.

FIG. 2 is a schematic cross-sectional view through a short length of one example of an instrument cable 104 in which an energy conveying structure and optical channel are combined in a compact manner. Generally speaking, the instrument cable 104 shown in FIG. 2 is a coaxial transmission line 125 having a hollow inner conductor that is capable of carrying an optical channel, which typically comprises one or more optical fibre bundles. The optical channel may thus be conveyed within the energy conveying means. This is in contrast to conventional surgical scoping devices, where an observation channel is typically formed separately from (i.e. outside) and parallel to an instrument channel.

In more detail, the coaxial transmission line 125 comprises an outer conductor 124, an inner conductor 128, and a dielectric material 126 separating the inner conductor 128 from the outer conductor 124. The inner conductor 128 may be formed on an innermost insulating conduit 130. The conduit 130 is hollow to define a central passage 132 along a longitudinal axis of the coaxial transmission line 125. The passage 132 is used to convey optical radiation as discussed further herein. The passage 132 may have a diameter 134 sized to receive the optical cable of a fiberscope. Such cables typically have a diameter of around 1 mm, so the passage may have a diameter of equal to or less than 1.5 mm, e.g. equal to or less than 1.2 mm.

An outer surface of the outer conductor 124 may be surrounded by a protective sheath 122. The sheath 122 may be flexible to enable manipulation, e.g. steering, of the instrument cable. The sheath 122 may be made from a biocompatible material or may have a biocompatible outer coating to enable the cable to be inserted directly into tissue. Any suitable material may be used, but PEEK is particularly preferred. As explained below, in some examples, the protective sheath 122 may be used to assist steering of the instrument tip.

Figure 3:
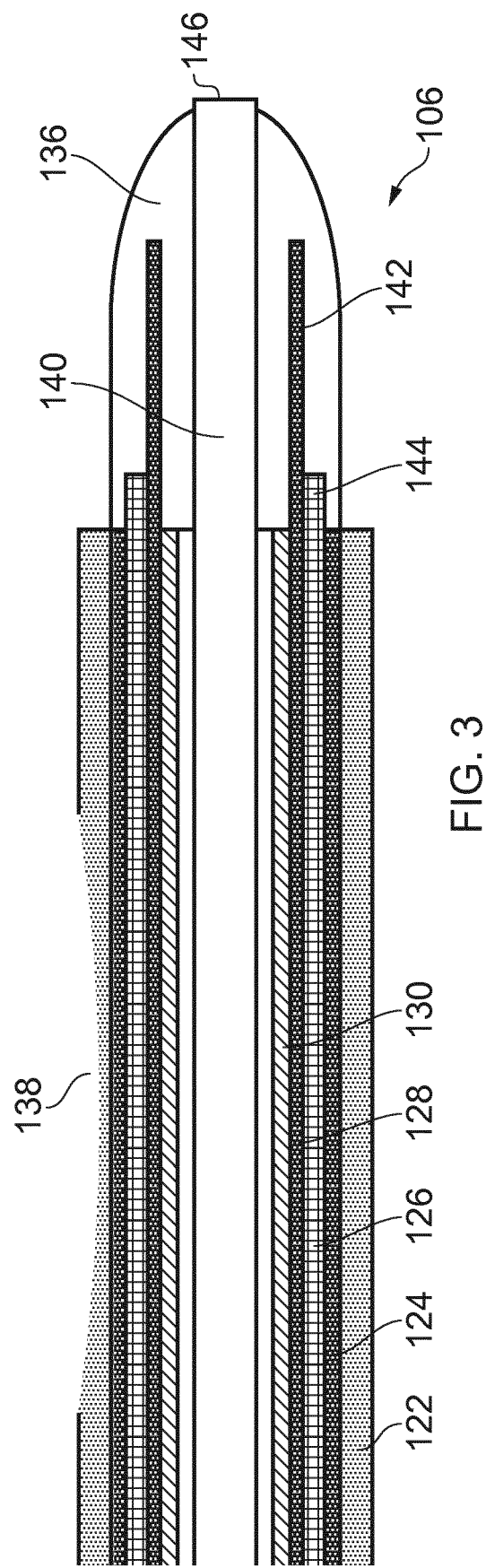
FIG. 3 is a schematic cross-sectional view through a first example distal end of an instrument cable and instrument tip of an electrosurgical apparatus that is an embodiment of the invention.

FIG. 3 is a schematic cross-sectional view through a distal end of a first example instrument cable 104. Features in common with FIG. 2 are given the same reference number and are not described again. In this example, the instrument tip 106 comprises a dome 136 of dielectric material that is attached (e.g. bonded or otherwise affixed) to the distal end of the instrument cable 104. The dome 136 may be made of a ceramic, or other similar material that can form a radiating antenna to delivery microwave EM energy received from the coaxial transmission line 125.

In this example, the inner conductor 128 has a distal portion 142 that extends distally beyond a distal end of the outer conductor 124. The distal portion 142 extends inside the dome 136. A suitable recess may be machined in the dome 136 to receive the distal portion 142. The dielectric material 126 may also having a distal portion 144 that extends beyond the distal end of the outer conductor. The distal portion 144 may provide an attachment surface for securing the dome 136 to the coaxial transmission line 125. The distal portion 142 of the inner conductor may extend beyond a distal end of the distal portion 144 of the dielectric material 126.

The dome 136 may have a bore formed therein which aligns with the passage 132 in the instrument cable 104 when the dome 136 is secured to the instrument cable. The bore terminates at a distal aperture 146 on the outer surface of the dome 136. An optical cable 140 is conveyed through the passage 132 and bore and terminates at the aperture 146. In a preferred embodiment, the optical cable 140 comprises an illumination fibre bundle for conveying an illumination signal from the handpiece to the treatment site. The illumination signal is optical radiation for illuminating or probing the treatment site, e.g. to make it visible for imaging or other types of optical sensing. The optical cable 140 may further comprise an imaging fibre bundle for carrying optical radiation from the treatment site, i.e. reflected or otherwise emitted from the treatment site, back to the handpiece, e.g. for detection.

In a development of the structure discussed above, the dome 136 may optionally include a transducer element suitable for transmitting ultrasonic energy to the treatment site. For example, the transducer element may be made from a piezoelectrically active ceramic. The instrument cable 104 may be arranged to deliver an operating voltage for the transducer element from the handpiece. In this arrangement, the apparatus may be capable for selective delivery of microwave, RF or ultrasonic energy for treatment in combination with an integrated system for visualizing the treatment site.

In FIG. 3, the protective sheath 122 is anchored at its distal end to the coaxial transmission line 125 by suitable bonding or physical connection (e.g. crimping or the like). The sheath 122 includes a cut-out portion 138 on one side thereof. The cut-out portion 138 may be a elongate oval or similar shape. The cut-out portion 138 defines a preferential lateral deformation axis for the sheath 122. In other words, it provides a structure weakness in the outer surface of the sheath 122 whereby when the sheath is put under compression it will preferentially bend over towards the side where the cut-out portion 138 is located. The cut-out portion 138 thus effectively acts as a living hinge.

Meanwhile, a proximal end of the sheath 122 is secured to a slider associated with the handpiece 102. The slider is movable relative to the handpiece through actuation of a steering mechanism. A proximal portion of the coaxial transmission line 125 is anchored so that it does not move relative to the handpiece. Movement of the slider therefore introduces a compressive or tensile force in the sheath relative to the coaxial transmission line, which in turn causes the instrument tip to bend or straighten in the sense defined by the living hinge.

In one example, bending of the instrument cable can be constrained within a distal portion thereof by making the protective sheath more rigid along its length expect at the distal portion. This can be done by providing a stiffening layer in or on the protective sheath. The stiffening layer may be provided by braiding on the protective sheath or by a jacket mounted over the instrument cable.

Figure 4:
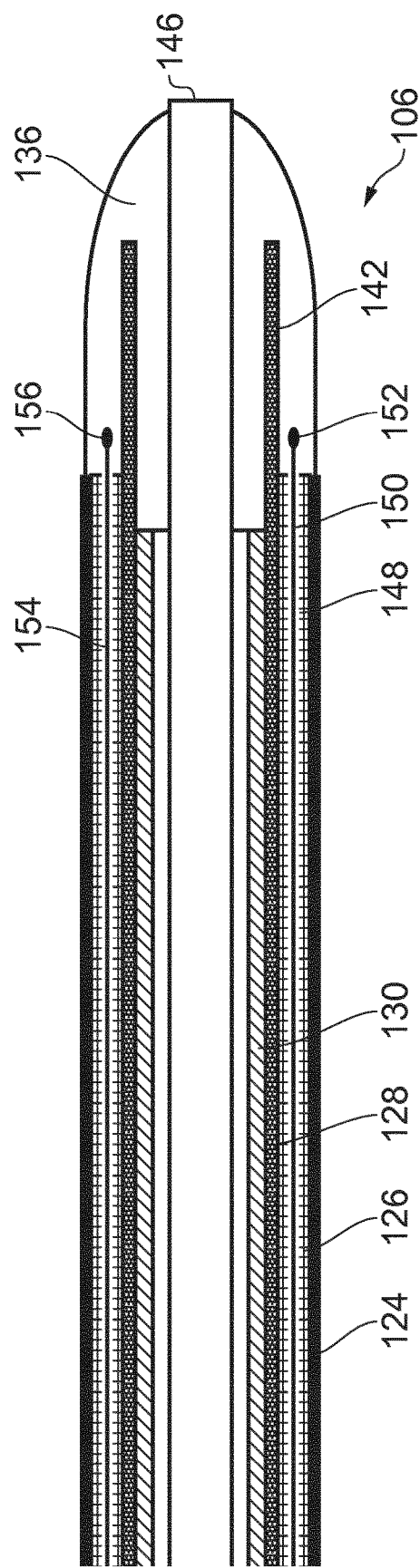
FIG. 4 is a schematic cross-sectional view through a second example distal end of an instrument cable and instrument tip of an electrosurgical apparatus that is an embodiment of the invention.

FIG. 4 is a schematic cross-sectional view through a distal end of a second example instrument cable 104. Features in common with FIG. 3 are given the same reference number and are not described again. In this example, the steering mechanism is incorporating into the dielectric material 126 of the coaxial transmission line 125. In principle these allows for removal of the protective sheath 122, which enables the instrument cable to have a smaller overall diameter. Although not shown in FIG. 4, there may still be a thin biocompatible coating formed on the outer surface of the outer conductor 124.

In FIG. 4 the steering is effected by one or more control wires 150, 154 that extend through the dielectric material 126 of the coaxial transmission line 125. The control wires 150, 154 may be made from a material having a similar dielectric constant to the dielectric material 126 to prevent them from disrupting the conveyed energy. For example, the control wires may be made from drawn PEEK fibre, whereas the dielectric material 126 may be an extruded PTFE tube or the like.

In this embodiment there are two control wires 150, 154 mounted on opposite sides of the instrument cable 104. There may be three of more control wires arranged around the circumference of the instrument cable to enable it to be steered in any direction. Each control wire 150, 154 is secured to the instrument tip (e.g. the dome 136) at a respective anchor point 152, 156.

Each control wire 150, 154 may be conveyed through a hole 148 formed in the dielectric material 126.

Similarly to the example discussed with reference to FIG. 3, the proximal end of each control wire 154, 156 is connected to a steering mechanism that is arranged to vary the linear position of the control wire with respect to the coaxial transmission line 125 (which may be fixed relative to the handpiece). Pulling the control wire back towards the handpiece causes the instrument cable to bend towards the side at which the anchor point for that control wire is located.

Figure 5:
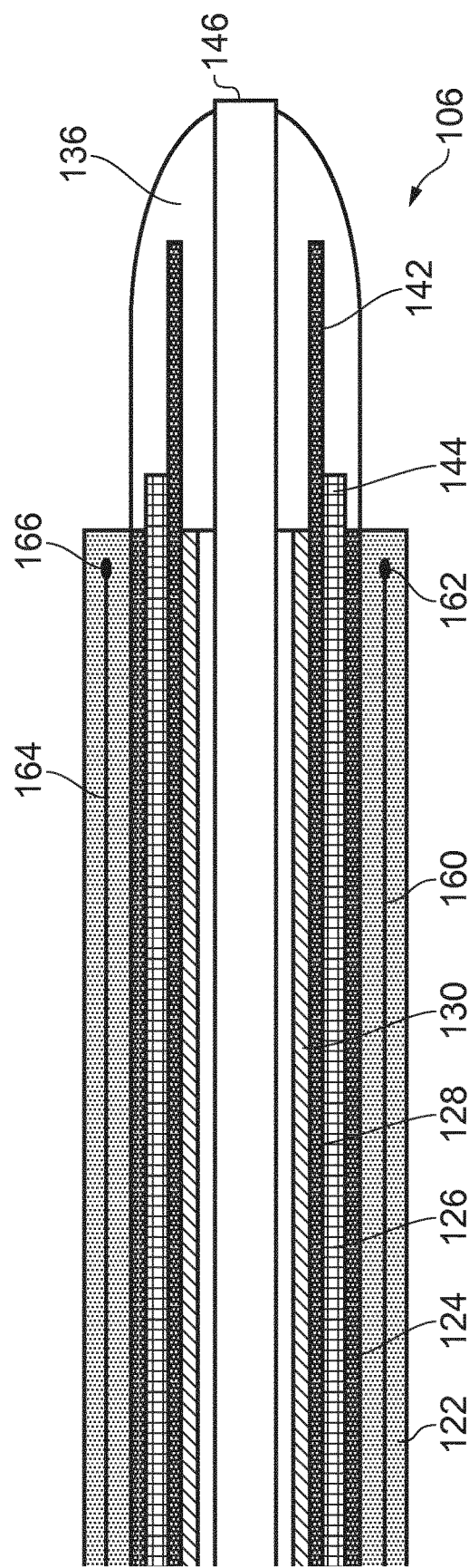
FIG. 5 is a schematic cross-sectional view through a third example distal end of an instrument cable and instrument tip of an electrosurgical apparatus that is an embodiment of the invention.

FIG. 5 is a schematic cross-sectional view through a distal end of a third example instrument cable 104. Features in common with FIG. 4 are given the same reference number and are not described again. The steering mechanism in FIG. 5 makes use of one or more control wires 160, 164 in a similar way to the example discussed with reference to FIG. 4. However, in this example, the control wires 160, 164 are mounted in the protective sheath 122 that surrounds the coaxial transmission line 125. The protective sheath 122 therefore comprises a multi-lumen tube, e.g. with a central lumen for conveying the coaxial transmission line and optical channel combination, and one or more outer lumens for conveying a respective control wire. Each control wire 160, 164 may be secured to the protective sheath 122 at a respective anchor point 162, 166 located at a distal end thereof.

Figure 6:
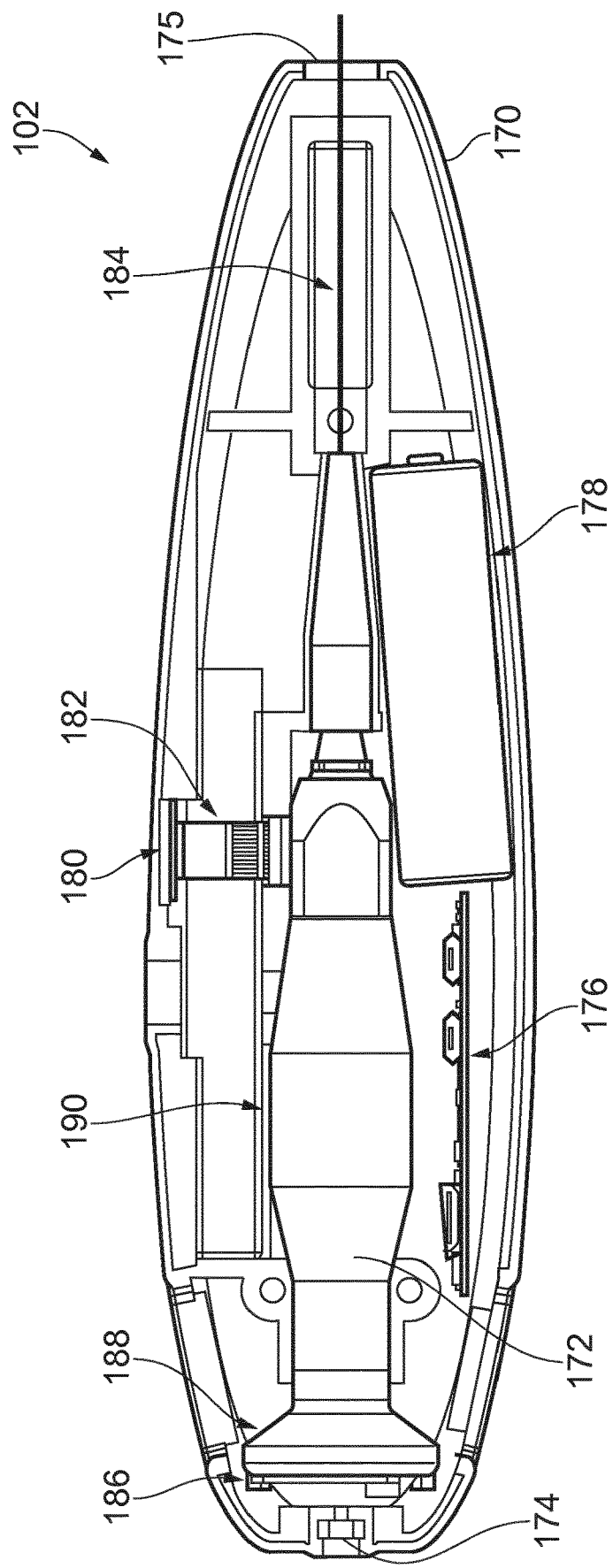
FIG. 6 is a cut-away side view showing internal optical components of a handpiece for an electrosurgical apparatus that is an embodiment of the invention.

FIG. 6 is a cut-away side view through the handpiece 102 to show some of the internal components. The handpiece 102 comprises a housing 170, which may be a hollow shell for containing the internal components. The housing 170 may have apertures in its outer surface to provide access either for a user to manipulate the components (e.g. for steering or focussing) or for energy to be coupled into the device. The housing 170 may comprises a plurality (e.g. two) portions which are securable together after the internal components are mounted therein.

Figure 7:
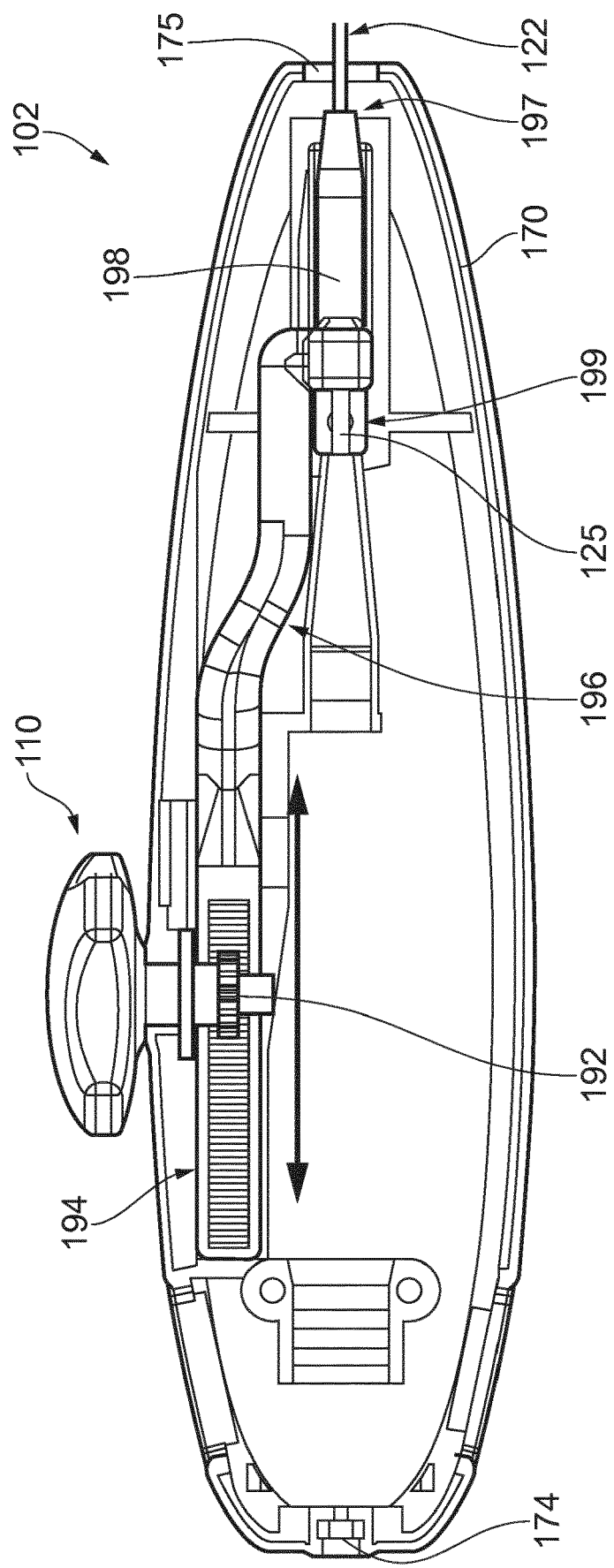
FIG. 7 is a cut-away side view showing a steering control mechanism mounted in a handpiece for an electrosurgical apparatus that is an embodiment of the invention.

In FIG. 6, for clarity only the optical components and associated power and control components are shown. FIG. 7 shows components for the steering mechanism. In addition to these components, the handpiece 102 carries the coaxial transmission line from the connector port 115 at the rear (proximal) end of the handpiece through a proximal aperture 174 and around the other internal components towards the cable 104.

The housing 170 has a fiberscope body 172 mounted therein, e.g. clipped into a recess formed in the housing to hold the fiberscope body 172 stationary relative to the housing 170. The fiberscope body comprises a front (distal) input light coupling portion that has a light input port 182 mounted thereon. A light source 180, which in this case is a surface mounted LED secured to an inside surface of the housing 170, is located across the light input port 182 to provide an illumination signal for the fiberscope. The front input light coupling portion couples the illumination signal into an illumination bundle of optical fibres which are carried in an optical channel 184 that passes within the instrument cable 104 (not shown). The housing 170 includes a front (distal) aperture 175 through which the instrument cable 104 (including the optical channel 184) passes out of the housing 170.

The optical channel 184 also includes an imaging bundle of optical fibres which convey optical radiation from the treatment site back to the fiberscope body 172. The imaging bundle typically has one or more micro-lenses at a distal end thereof to focus the optical radiation from the treatment site into the imaging bundle. The fiberscope body 172 comprises a set of optical elements (e.g. lenses) that are arranged to focus optical radiation received from the imaging bundle to allow it to be viewed through a viewport at the rear (proximal) end of the fiberscope body 172. The fiberscope body 172 may include a focus adjuster 190 for varying the focal length of the set of optical elements. The focus adjuster 190 may be a rotatable barrel. The housing may include a window in a side surface thereof to allow an operator to contact and rotate the barrel.

In the arrangement shown in FIG. 6, the viewport is in optical communication with an output lens arrangement 188 that focuses an image onto an image sensor 186 (e.g. a digital camera or other suitable device for converting optical radiation into an encoded image). In one example, the conventional output optics found in the viewport of a fiberscope may be replaced by a reverse fisheye lens that acts to spread the optical radiation received from the imaging bundle over a sensing area of the image sensor 186.

A controller 176 is mounted in the housing 170. The controller 176 may be operably connected to the image sensor 186 and the light source 180 to control operation of the fiberscope. The controller 176 may comprise a microprocessor or a single board computer, such as a Raspberry Pi or the like. As discussed below with reference to FIG. 8, the controller 176 may also be operably connected to a transceiver for communicating images captured by the image sensor 186 to a remote device for display.

The housing 170 may include a power source 178 such as a cell or battery. In one example, the power source 178 comprises a 18650 lithium ion cell or the like. The power source 178 may be rechargeable, e.g. through a suitable charging port located in an outer surface of the housing 170. The power source 186 may provide energy to operate the light source 180, the controller 176, the image sensor 186 and the transceiver (not shown). The handpiece 102 may include an ON/OFF switch to activate and deactivate the device in order to conserve power when the apparatus is not in use.

The fiberscope discussed above with reference to FIG. 6 may resemble a conventional fiberscope device, albeit with its eyepiece replaced by the output lens arrangement 188 and image sensor 186.

FIG. 7 is a cut-away side view through the handpiece 102 to show internal components that provide steerability to the instrument cable. Features in common with examples discussed above are given the same reference number and are not described again. As shown in FIG. 7, the housing 170 may comprises a steering mechanism that is based on a rack and pinion to transform rotation motion of the rotatable knob 110 into longitudinal sliding motion of the protective sheath 122 with respect to the coaxial transmission line 125.

The rotatable knob 110 is rotatably mounted on the housing 170 by a shaft which is retained in an aperture formed in the housing 170 by a flange. The shaft extends below the flange to provide a pinion gear 192 that is operably engaged with a rack 194 that is slidably mounted within the housing 170. The portion of the rotatable knob 110 that is located outside the housing 170 may have a grip shaped to assist rotation.

The rack 194 is slidable in a longitudinal direction, i.e. in a direction substantially aligned with or parallel to the axial direction of the coaxial transmission line. The rack 194 is operably connected to or formed integrally with a push arm 196. The push arm 196 comprises a collar 198 that fits over a proximal portion of the instrument cable 104. In this example, the collar 198 is attached to the protective sheath 122 of the instrument cable 104, e.g. at an attachment point 197. Meanwhile, the coaxial transmission line 125 is fixed relative to the housing 170 at an anchor point 199. Longitudinal movement of the collar 198 relative to the housing therefore introduces a relative force between the coaxial transmission line 125 and the protective sheath 122 to cause bending at the distal end of the instrument cable 104 as discussed above with reference to FIG. 3.

In other examples, the push arm 196 may be connected to one or more control wires that extend through the instrument cable in the manner discussed with reference to FIGS. 4 and 5. In these examples, a proximal portion of the coaxial transmission line remains fixed relative to the housing, but it may not be necessary for the push arm 196 to be secured to the protective sheath 122.

In some examples, the anchor point 199 may have a dual function. Firstly it may secure a proximal portion of the coaxial transmission line to the housing in the manner discussed above. Secondly it may comprise a transformer for interconnecting a first energy conveying structure (which may be a conventional coaxial cable) that extends between the connector port 115 at the input aperture 174 and the anchor point 199 with a second energy conveying structure, which is the hollow coaxial transmission line 125 that extends along the instrument cable 104. In some examples, an impedance of the coaxial transmission line 125 may be different from an impedance of the first energy conveying structure. The transformer may provide an impedance matching function to reduce or eliminate energy losses within the handpiece 102.

Figure 8:
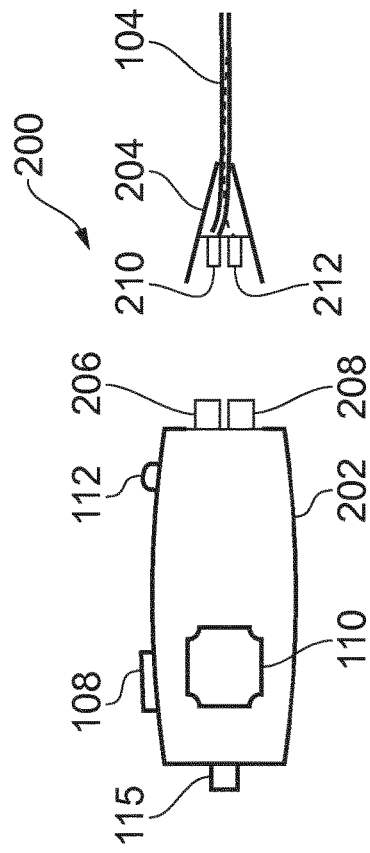
FIG. 8 is a schematic diagram of a handpiece with detachable cable that can be used in an electrosurgical apparatus that is an embodiment of the invention.

FIG. 8 is a schematic diagram of another example of a handpiece 200 that can be used in an electrosurgical apparatus that is an embodiment of the invention. Features in common with the handpiece 102 described above are given the same reference number and are not described again. The handpiece 200 depicts a schematic example of an embodiment in which the instrument cable 104 may be a detachable and, optionally, disposable item.

The handpiece 200 comprises a main body 202 which houses the internal components discussed above with respect to FIGS. 6 and 7. At a front (distal) end of the main body 202, there are two connection ports 206, 208. A first connection port 206 is for transferring the microwave and/or RF energy from the main body 202 into the instrument cable 104. A second connection port 208 is for transferring the optical radiation to and/or from the instrument cable 104. The first connection port 206 may be QMA port or the like. The second connection port 208 may be an optical coupler or fiberscope connector.

The instrument cable 104 in this example may have a proximal end case 204 that is arranged to engage with and attach to a distal portion of the main body 202. In this example, the proximal end case 204 may also act as a deflection limiting means for the instrument cable 104 to prevent it from experience too much bending at the handpiece. The proximal end case 204 may comprises engagement features (not shown), e.g. on an inner surface thereof, which cooperate with corresponding features on the main body 202 to secure the two parts together.

The proximal end case 204 may define a recess in which a pair of connectors 210, 212 are mounted. A first connector 210 may be receivable in the first connector port 206 when the proximal end case 204 is mounted on the main body 202. The first connector 210 is a proximal terminus of the coaxial transmission line 125 that is conveyed by the instrument cable 104. When the first connector 210 is operably connected to the first connector port 206, microwave and/or RF energy from the main body 202 can be transferred into the instrument cable 104.

A second connector 212 may be receivable in the second connector port 208 when the proximal end case 204 is mounted on the main body 202. The second connector 212 is a proximal terminus of a optical channel 140 that is conveyed by the instrument cable 104. When the second connector 212 is operably connected to the second connector port 208, optical radiation can be transferred into and out of the instrument cable 104.

Figure 9:
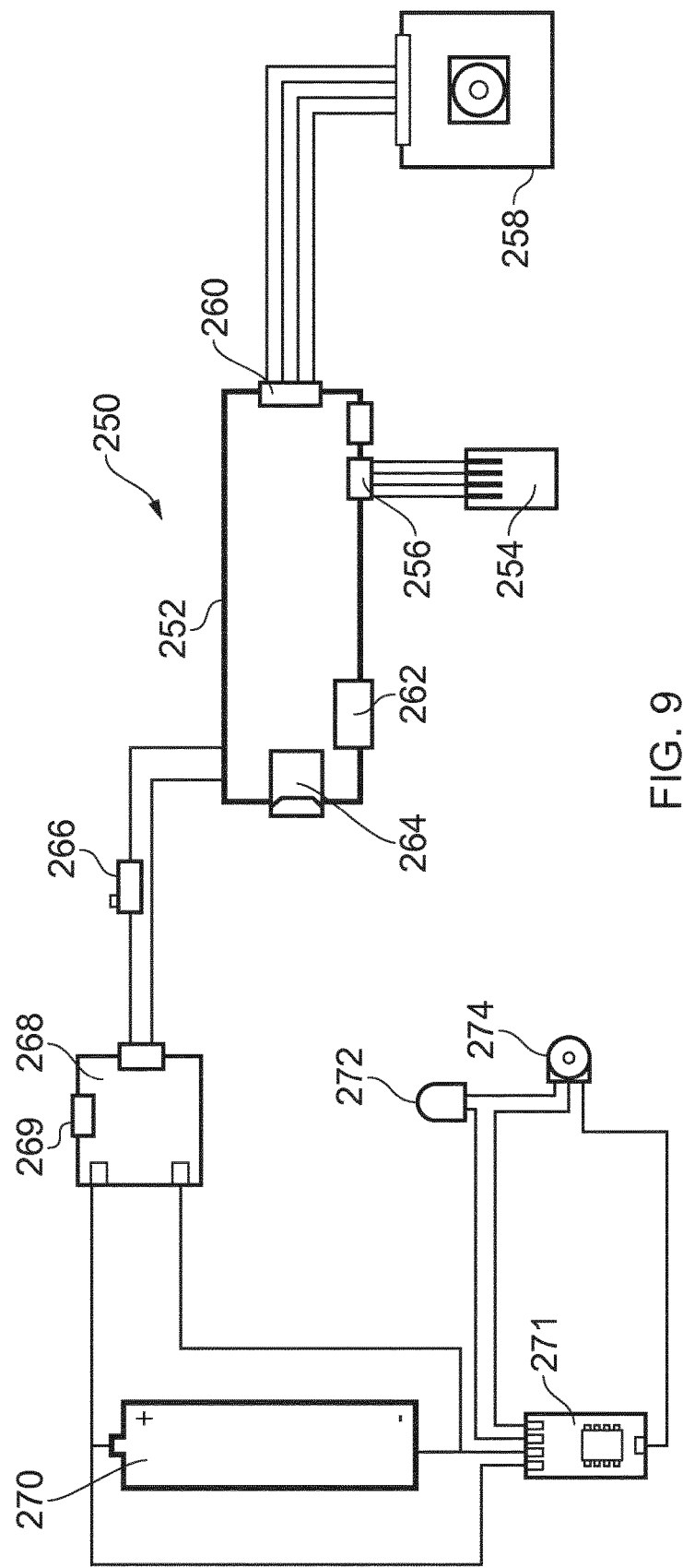
FIG. 9 is a schematic circuit diagram of the optical components within a handpiece for an electrosurgical apparatus that is an embodiment of the invention.

FIG. 9 is a schematic circuit diagram of a circuit arrangement 250 within a handpiece for an electrosurgical apparatus that is an embodiment of the invention. The circuit arrangement comprises a controller 252, which may be a microprocessor or a single board computer such as a Raspberry Pi or the like. The controller 252 is connected to control an image sensor 258 through a first interface 260. In this example, the image sensor 258 is an 8 megapixel camera. The controller 252 is also connected to a transceiver 254 via a second interface 256. For example, the transceiver 254 may be a USB WiFi dongle connected to the microprocessor via a micro USB port or the like. This arrangement forms an output circuit for capturing and transmitting or broadcasting images from the fiberscope. The controller 252 may have a memory with software instructions stored thereon which, when executed, cause the controller to record images using the camera and to display those images on a remote display device, e.g. a computer, tablet or smart phone. In one example, the device may broadcast to a local wireless hotspot to which other devices can connect. A user can navigate to a specific URL (e.g. 192.168.42.1/vision.php) to access the images. Further information can also be shown on the display, including patient information, date/time and any other information required.

In a development of the arrangement shown in FIG. 9, the controller 252 may communicate with a user interface to enable functionality and operation to be controlled or modified on the fly. The user interface may be on the handpiece itself, e.g. as a series of buttons and a display to show current operational status and modification operations. Alternatively or additionally, the user interface may be on a remote device that is in networked communication with the controller 252 via the transceiver 254. The controller 252 may thus be operated remotely. Examples of on the fly control include modifications such as image brightness, contrast and sharpness, and switching between recording of still images and video.

Where the controller 252 is a single board computer, it may comprise ports that are not used, for example a mini HDMI interface 262 and a micro SD interface 264.

The circuit arrangement 250 comprises a power source 270, which may be a rechargeable cell or the like, connected to the controller 252 via a charging circuit 268. The charging circuit is arranged to regulate voltage. It may include a connector port 269, e.g. a micro USB socket, to enable the circuit arrangement to be connect to a mains supply to allow for recharging the power source. in one example, the power source 270 is a 18650 lithium ion cell, and the charging circuit is arranged to provide both a voltage increase and regulation (typically from 3.7-4.2 V to 5 V). An ON/OFF switch 266 may be provided on the connection between the charging circuit 268 and the controller 252.

The circuit arrangement 250 further comprises a constant current circuit 271 connected between the power source 270 and a light source 272. In this example, the light source is an LED. It may be desirable to vary the illumination level at the treatment site, so the circuit further comprises a potentiometer 274 to allow the LED to be dimmable. The potentiometer 274 may have an actuator associated with it that is accessible to the user through an aperture on the outside of the handpiece. The actuator may be a thumbwheel, slider or any other suitable control element. The constant current circuit 271 is arranged to ensure that the light source 272 only pulls a limited current (e.g. approximately 500 mA) from the power source 270. This is to both conserve charge but to also minimise the risk of higher current levels causing unwanted heating within the handpiece.

The circuit arrangement 250 and apparatus discussed above may be combined into a particular example as follows. The main assembly of the handpiece may comprise a fiberscope with a 1 mm optical channel having both send and return fibre bundles and an integrated lens assembly at the proximal end. The optical channel may be housed within a hollow coaxial transmission line along which microwave power can be delivered. The coaxial transmission line may terminate at a distal cylindrical ceramic (e.g. Macor) radiating tip with a rounded end and concentric hole for vision through the fibre.

The image from the fiberscope may be magnified using a fish-eye lens in reverse, and captured via a camera and processed through a single board computer processor (such as a Raspberry Pi Zero), zoomed digitally and broadcast or uploaded for access via WiFi. A lithium-ion cell or battery can power the processor and a single LED light-source fed into a light-port on the fiberscope lens assembly in order to illuminate the body cavity at the distal end of the vision system.

The main assembly may be encapsulated within a plastic vacuum-cast handpiece. Although this example operates using a conventional fiberscope, this is not essential. In other example a dedicated lens assembly may be built directly into the handpiece.

The light source may be arranged to mimic daylight as closely as possible, as this would be best for illuminating the treatment site, and would closely mimic the halogen sources with which bronchoscopic surgeons are accustomed. The LED used may thus be a white light LED having around 5.8 Kelvin colour temperature. The LED may have an output of around 50-100 lumens in order to sufficiently illuminate the treatment site.

The combined optical channel and coaxial transmission line may be housed inside a protective sheath (e.g. made from PEEK), and may be steerable with one degree of freedom based upon a living-hinge type mechanism. To provide predictable steering, a length of material may be removed from one side of the protective sheath at its distal end such that it creates a weakness. The sheath have be secured to the combined optical channel and coaxial transmission line at its distal end. When sheath is pushed or pulled from the proximal end, the distal end is therefore forced to bend, allowing movement and vision around corners.

To prevent ingress of fluids, the protective sheath may be covered in heat-shrink tubing. The instrument cable may have a maximum outer diameter equal to or less than exceed 3.5 mm. The heat-shrink tubing may act to hold the assembly together so that the protective sheath does not exceed its elastic limit and permanently deform.

At the proximal end, the handpiece may have a rotatable knob or handle which, when turned, causes the protective sheath to move back and forth along the length of the coaxial transmission line, providing the steering capability.

Other steering mechanisms may be used. For example, a control wire (e.g. made from nitinol) may be fed between the outer conductor of the coaxial transmission line and an inner surface of the protective sheath. The control wire may be fastened on an outer surface of the protective sheath at its distal end. The control wire may run through fixed guides on the outer surface of the coaxial transmission line so as to reliably pull in any given direction. There may be a plurality of control wires. Each control wire may be fixed to a rotary barrel at the proximal end of the instrument cable. When the barrel is rotated in a first sense, a first control wire may be pulled in one direction while a second control wire is released in the other direction. This can provide steering about one axis at the distal end. Further two wires could be added to give another axis of movement, which when combined could give full 360-degree steerability.

The invention claimed is:

1. An electrosurgical device for performing invasive electrosurgery, the electrosurgical device comprising:
a handpiece;
an instrument cable connected to and extending away from the handpiece, the instrument cable comprising a coaxial layered energy conveying structure having:
an inner conductive layer;
an outer conductive layer formed coaxially with the inner conductive layer;
a dielectric layer separating the inner conductive layer and the outer conductive layer; and
a protective sheath on an outer surface of the outer conductive layer,
wherein the protective sheath comprises a distal portion and a proximal portion, wherein the proximal portion is configured to have greater rigidity than the distal portion,
wherein the inner conductive layer, the outer conductive layer and the dielectric layer form a coaxial transmission line for conveying radiofrequency (RF) or microwave electromagnetic (EM) energy,
wherein the inner conductive layer is hollow to form a longitudinal passage, and
wherein the energy conveying structure further comprises an optical channel for conveying optical radiation, the optical channel being located in the longitudinal passage, and comprising:
an illumination optical fibre bundle for conveying an illumination signal along the optical channel in a first direction, and
an imaging optical fibre bundle for conveying an imaging signal along the optical channel in a second direction; and
an instrument tip comprising a piece of dielectric material mounted at a distal end of the instrument cable,
wherein the instrument tip is connected to the coaxial transmission line to deliver the radiofrequency (RF) or microwave EM energy out of the electrosurgical device,
wherein the inner conductive layer extends longitudinally into the piece of dielectric material beyond a distal end of the outer conductive layer to form a radiating antenna for the microwave EM energy, and
wherein the handpiece comprises:
one or more optical elements arranged to optically control or manipulate optical radiation transmitted into or received from the optical channel; and
a steering mechanism for controlling an orientation of a distal portion of the instrument cable, wherein the steering mechanism comprises:
an actuator mounted on an outer surface of the handpiece;
a pull arm operably coupled to the actuator to slide within the handpiece; and
a control element extending along the instrument cable, the control element being operably coupled to the pull arm and the distal portion of the instrument cable, wherein the control element comprises the protective sheath that surrounds the coaxial layered structure, wherein the protective sheath is anchored to the coaxial layered structure at the distal portion of the instrument cable and free to move relative to the coaxial layered structure at the handpiece, and wherein the coaxial layered structure is anchored to the handpiece; and
wherein a proximal end of the protective sheath is secured to a slider associated with the handpiece, and
wherein the slider is movable relative to the handpiece through actuation of the steering mechanism so that movement of the slider introduces a compressive or tensile force in the protective sheath relative to the coaxial layered structure.

2. An electrosurgical device according to claim 1 dimensioned to be insertable in a flexible insertion tube of an invasive surgical scoping device.

3. An electrosurgical device according to claim 1 having a maximum outer diameter equal to or less than 3.5 mm.

4. An electrosurgical device according to claim 1, wherein the coaxial layered energy conveying structure comprises an innermost insulating layer between the inner conductive layer and the optical channel.

5. An electrosurgical device according to claim 1, wherein the optical channel extends through a bore in the instrument tip.

6. An electrosurgical device according to claim 1, wherein the optical channel terminates at an aperture formed in an outer surface of the instrument tip.

7. An electrosurgical device according to claim 1, wherein the piece of dielectric material is a cylindrical piece of ceramic with a rounded distal tip.

8. An electrosurgical device according to claim 1, wherein the handpiece further comprises a light source for generating the illumination signal.

9. An electrosurgical device according to claim 8, wherein the light source is a light emitting diode.

10. An electrosurgical device according to claim 1, wherein the handpiece comprises a fiberscope body, and wherein the optical channel comprises an insertion tube of the fiberscope.

11. An electrosurgical device according to claim 1, wherein the control element comprises one or more control wires that are attached to the pull arm and secured to the instrument cable at the distal portion thereof.

12. An electrosurgical device according to claim 11, wherein the control wires extend longitudinally through the dielectric layer of the coaxial transmission line.

13. An electrosurgical device according to claim 11, wherein the control wires extend longitudinally through a protective sheath that surrounds the coaxial layered structure.

14. An electrosurgical device according to claim 1, wherein the handpiece comprises a power source.

15. An electrosurgical device according to claim 14, wherein the power source is rechargeable.

16. An electrosurgical device according to claim 1, wherein the handpiece comprises a housing for enclosing its internal components.

17. An electrosurgical device according to claim 16, wherein the instrument cable is detachable from the housing.

18. An electrosurgical device according to claim 1, wherein the instrument tip comprises an ultrasonic transducer arranged to couple an ultrasonic signal into biological tissue.

19. An electrosurgical device according to claim 18, wherein the instrument tip comprises a piezoelectrically active ceramic, and the instrument cable is arranged to convey a voltage signal for controlling the piezoelectrically active ceramic to generate the ultrasonic signal.

20. An electrosurgical device according to claim 1, wherein the handpiece comprises an optical sensor for detecting optical radiation received into the handpiece from the optical channel.

21. An electrosurgical device according to claim 20, wherein the optical sensor is an image sensor for generating a digital image of a treatment site located at a distal end of the optical channel based on an imaging signal received into the handpiece from the optical channel.

22. An electrosurgical device according to claim 21, wherein the image sensor is a digital camera.

23. An electrosurgical device according to claim 20, wherein the handpiece comprises a communication module arranged to communicate information relating to the detected optical radiation to a remote device.

24. An electrosurgical device according to claim 23, wherein the communication module comprises a transceiver that is communicably connectable to a wireless network.

25. An electrosurgical device according to claim 23, wherein the communication module is arranged to upload image data to a remote server.

26. An electrosurgical apparatus comprising:
an electrosurgical device according to claim 23; and
a display device arranged to receive and display the information relating to the detected optical radiation.

27. An electrosurgical apparatus according to claim 26, wherein the display device is a laptop computer, tablet computer, or smartphone.

28. An electrosurgical system comprising:
an electrosurgical generator arranged to generate RF or microwave EM energy; and
an electrosurgical device according to claim 1,
wherein the handpiece is connected to the generator to receive the RF or microwave EM energy and couple it into the coaxial transmission line in the instrument cable.

29. An electrosurgical device according to claim 1, wherein the protective sheath has a cut-out portion at one side thereof in the distal portion of the instrument cable.

30. An electrosurgical device for performing invasive electrosurgery, the electrosurgical device comprising:
a handpiece;
an instrument cable connected to and extending away from the handpiece, the instrument cable comprising a coaxial layered energy conveying structure having:
an inner conductive layer;
an outer conductive layer formed coaxially with the inner conductive layer;
a dielectric layer separating the inner conductive layer and the outer conductive layer; and
wherein the inner conductive layer, the outer conductive layer and the dielectric layer form a coaxial transmission line for conveying radiofrequency (RF) and/or microwave electromagnetic (EM) energy,
wherein the inner conductive layer is hollow to form a longitudinal passage, and
wherein the energy conveying structure further comprises an optical channel for conveying optical radiation, the optical channel being located in the longitudinal passage; and
an instrument tip comprising a piece of dielectric material mounted at a distal end of the instrument cable,
wherein the instrument tip is connected to the coaxial transmission line to deliver the radiofrequency (RF) and/or microwave EM energy out of the electrosurgical device, and
wherein the handpiece comprises a steering mechanism for controlling an orientation of a distal portion of the instrument cable,
wherein the steering mechanism comprises:
an actuator mounted on an outer surface of the handpiece;
a pull arm operably coupled to the actuator to slide within the handpiece and
a control element extending along the instrument cable, the control element being operably coupled to the pull arm and the distal portion of the instrument cable,
wherein the control element comprises a protective sheath that surrounds the coaxial layered structure, wherein the protective sheath is anchored to the coaxial layered structure at the distal portion of the instrument cable and free to move relative to the coaxial layered structure at the handpiece, and wherein the coaxial layered structure is anchored to the handpiece,
wherein a proximal end of the protective sheath is secured to a slider associated with the handpiece, and
wherein the slider is movable relative to the handpiece through actuation of the steering mechanism so that movement of the slider introduces a compressive or tensile force in the protective sheath relative to the coaxial layered structure.

* * * * *